(12) United States Patent
Li et al.

(10) Patent No.: US 9,894,934 B2
(45) Date of Patent: Feb. 20, 2018

(54) AEROSOL GENERATING DEVICE AND AEROSOL INHALATION DEVICE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Yansheng Zhang, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 511 days.

(21) Appl. No.: 14/604,751

(22) Filed: Jan. 26, 2015

(65) Prior Publication Data

US 2015/0208730 A1    Jul. 30, 2015

(30) Foreign Application Priority Data

Jan. 26, 2014    (CN) ...................... 2014 2 0049360 U

(51) Int. Cl.
*A24F 47/00* (2006.01)
*A61M 15/06* (2006.01)

(52) U.S. Cl.
CPC ........... *A24F 47/008* (2013.01); *A61M 15/06* (2013.01)

(58) Field of Classification Search
CPC ..................................................... A24F 47/008
See application file for complete search history.

(56) References Cited

U.S. PATENT DOCUMENTS

| 2008/0092912 A1* | 4/2008 | Robinson | A24F 47/008 131/200 |
| 2013/0220315 A1* | 8/2013 | Conley | A24F 47/008 128/202.21 |

\* cited by examiner

*Primary Examiner* — Anthony Calandra
(74) *Attorney, Agent, or Firm* — Cheng-Ju Chiang

(57) ABSTRACT

The present disclosure relates to an exemplary aerosol generating device for heating a tobacco block. The aerosol generating device includes a shell, a mouthpiece assembly at an end of the shell, and an atomizing assembly received in the shell. The atomizing assembly includes a hollow heating body configured for inserting into the tobacco block. The heating body includes an inner surface and an outer surface for heating the tobacco block.

19 Claims, 7 Drawing Sheets

AEROSOL GENERATING DEVICE AND AEROSOL INHALATION DEVICE HAVING SAME

TECHNICAL FIELD

The present invention relates to aerosol inhalation devices, and particularly to an aerosol generating device and an aerosol inhalation device using same.

BACKGROUND ART

A typical electronic cigarette includes an atomizer and a battery assembly. The atomizer includes an atomizing sleeve, a liquid reservoir defined in the atomizing sleeve, and a heating component. The liquid reservoir is configured for storing tobacco liquid. The heating component is for heating the tobacco liquid to form aerosol. However, the aerosol may do not taste as good as that of ordinary cigarette.

What is needed, therefore, is an aerosol generating device and an aerosol inhalation device using same, which can overcome the above shortcomings.

SUMMARY

The present disclosure relates to an exemplary aerosol generating device for heating a tobacco block. The aerosol generating device includes a shell, a mouthpiece assembly at an end of the shell, and an atomizing assembly received in the shell. The atomizing assembly includes a hollow heating body configured for inserting into the tobacco block. The heating body includes an inner surface and an outer surface for heating the tobacco block.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
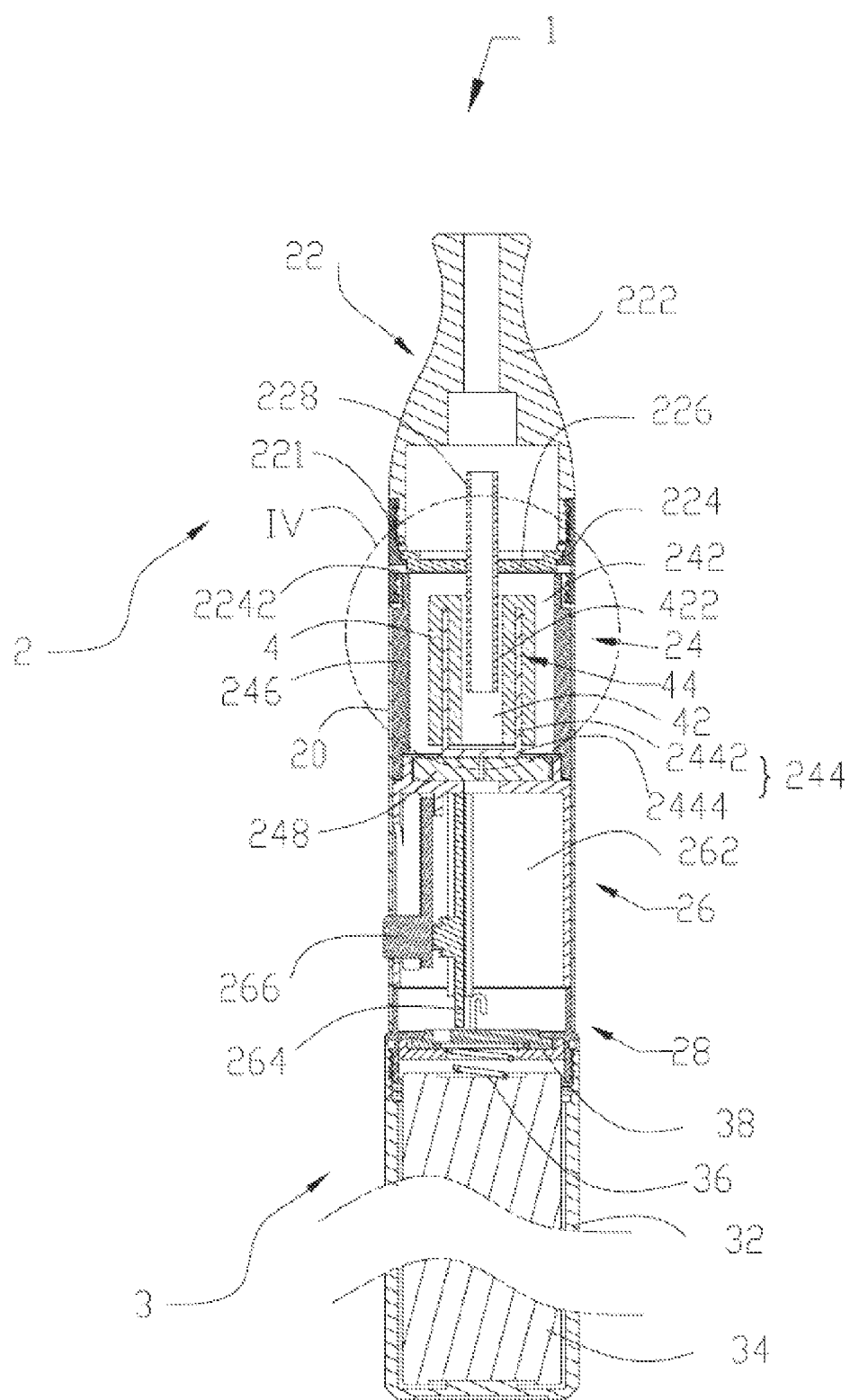
FIG. 1 is a cross-section view of an aerosol generating device according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
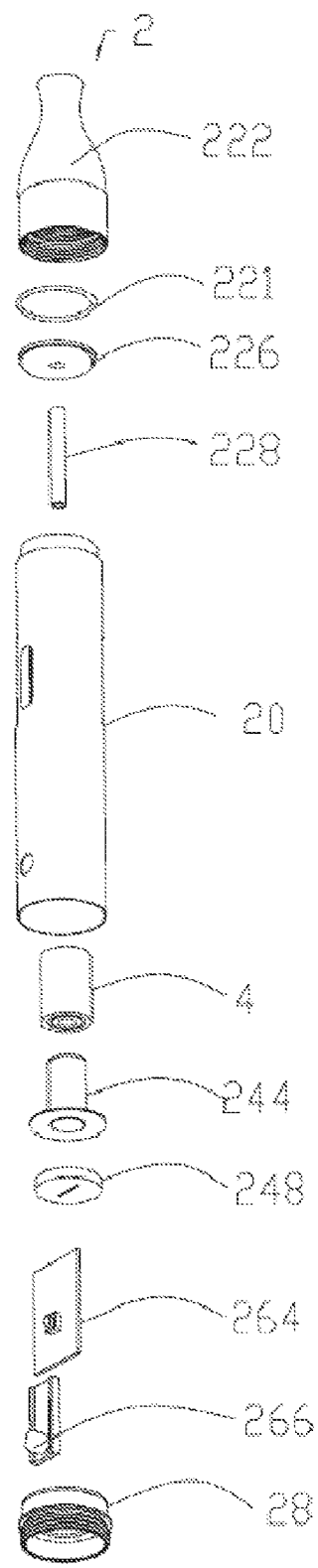
FIG. 2 is an isometric exploded view of the aerosol generating device of FIG. 1.

Referring to FIGS. 1-2, an aerosol inhalation device 1 includes an aerosol generating device 2 and a power supply 3 detachably connected to the aerosol generating device 2. In the present embodiment, the aerosol generating device 2 are coupled to the power supply 3 via screw threads. The power supply 3 is configured (i.e., structured and arranged) for providing power to the aerosol generating device 2. The power supply 3 may be a battery.

The aerosol generating device 2 includes a shell 20, a mouthpiece assembly 22, an atomizing assembly 24, a circuit board assembly 26, and a connecting assembly 28. The mouthpiece assembly 22 and the connecting assembly 28 are arranged at two opposite ends of the shell 20. The atomizing assembly 24 and the circuit board assembly 26 are both received in the shell 20. The atomizing assembly 24 is adjacent to the mouthpiece assembly 22, while the circuit board assembly 26 is adjacent to the connecting assembly 28.

The mouthpiece assembly 22 includes a mouthpiece 222, a connecting element 224 fixedly connected with the mouthpiece 222, a thermal baffle 226 arranged at an end of the mouthpiece 222, an air pipe 228 passing through the thermal baffle 226, and a gasket 221 between the mouthpiece and the thermal baffle 226. The connecting element 224 is configured for detachably connecting the mouthpiece 222 and the shell 20, e.g., threadedly. The air pipe 228 communicates with the mouthpiece 222. The connecting element 224 defines a plurality of air inlets 2242 in a side surface thereof. It is to be noted that the connecting element 224 and the mouthpiece 222 may be integrally formed.

The atomizing assembly 24 includes an atomizing chamber 242 defined in the shell 20, a hollow heating body 244 accommodated in the atomizing chamber 242. The air inlets 2242 communicates with the atomizing chamber 242. The heating body 244 is for heating a tobacco block 4. The heating body 244 includes a base 2444 and a heating wall 2442 extending substantially vertically from the base 2444. In the present embodiment, the heating wall 2442 is cylindrical. It is to be understood that, in other embodiments, the heating wall 2442 can be other shape, e.g., square, and a shape of the tobacco block 4 should be changed accordingly.

Figure 3:
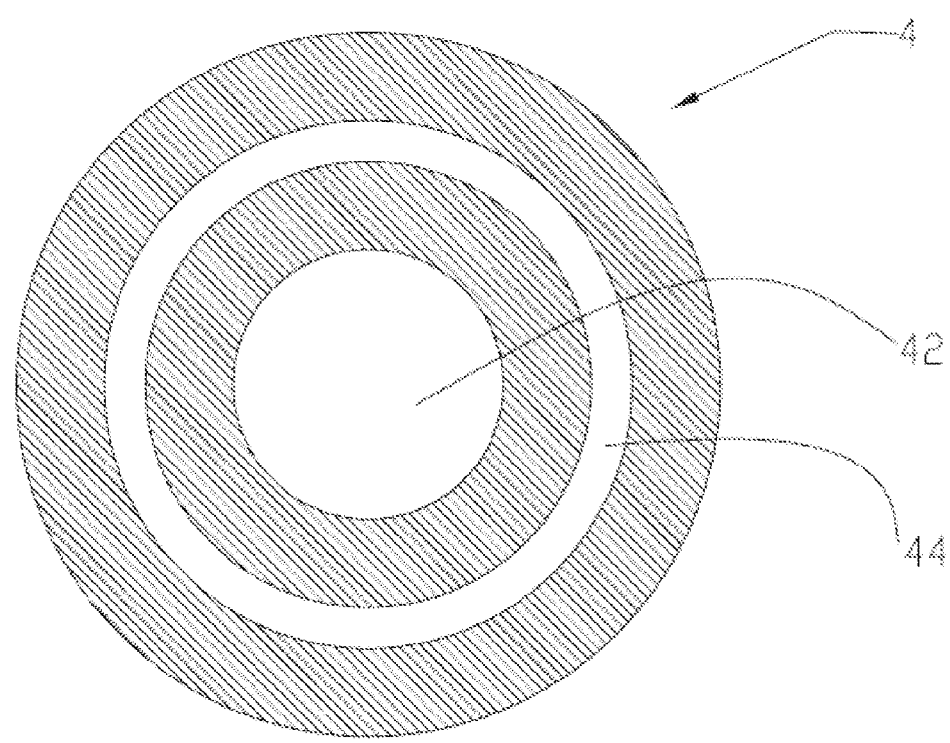
FIG. 3 is a schematic plan view of an end of a tobacco block according to the first embodiment.

Referring to FIG. 3, the tobacco block 4 is substantially cylindrical, and defines a cylindrical through hole 42. The tobacco block 4 further defines a cylindrical groove 44 at one end, and is double ring shaped in cross section. The air pipe 228 inserts into the through hole 42 of the tobacco block 4, and the air pipe 228 and an internal surface of the tobacco block 4 cooperatively define a first air passage 422.

The heating wall 2442 inserts the groove 44, an inner surface and an outer surface of the heating wall 2442 are both adapted for heating the tobacco block 4. Quite usefully, the inner surface and the outer surface of the heating wall 2442 are in surface contact with the tobacco block 4, so as to heat the tobacco block 4 more evenly. To improve user experience, a heat insulation ring 246 is provided on a side surface of the atomizing chamber 242, and a heat insulation cotton 248 is provided at an end of the atomizing chamber 242 away from the mouthpiece assembly 22.

The circuit board assembly 26 includes a heat insulation chamber 262 in the shell 20, a printed circuit board (PCB) 264 in the heat insulation chamber 264, and a switch button 266. The switch button 266 protrudes out of the shell 20. The switch button 266 and the PCB 264 are configured for controlling the aerosol generating device 2 to work. The heat insulation cotton 248 prevents heat generated in the atomizing chamber 242 from affecting the PCB 264. Furthermore, the heat insulation chamber 262 serves as a heat buffer. The heat from the atomizing chamber 242 is further decreased after passing the heat insulation chamber 262, thus reducing effects of the heat on the power supply 3.

The connecting assembly 28 is arranged at one end of the shell 20 away from the mouthpiece 222, and configured for detachably connecting with the power supply 3. In the present embodiment, the connecting assembly 28 and the power supply 3 are coupled via screw threads.

The power supply 3 includes a casing 32, a battery 34 received in the casing 32, a spring 36 in contact with the battery 34, a holder 38 for supporting the spring 36.

In use, the mouthpiece assembly 22 is screwed off from the shell 20, and the tobacco block 4 is placed into the atomizing chamber 242 in such a manner that the heating wall 2442 inserts the cylindrical groove 44. Then the mouthpiece assembly 22 is coupled to the shell 20, the switch button 266 is pressed, and the heating body 244 starts heating. The tobacco block 4 is heated and baked to form aerosol, and aerosol passes the mouthpiece 222 to reach the user. After the tobacco block 4 is finished, the mouthpiece 222 is screwed off from the shell 20 to replace the used tobacco block 4 with a new tobacco block.

Figure 4:
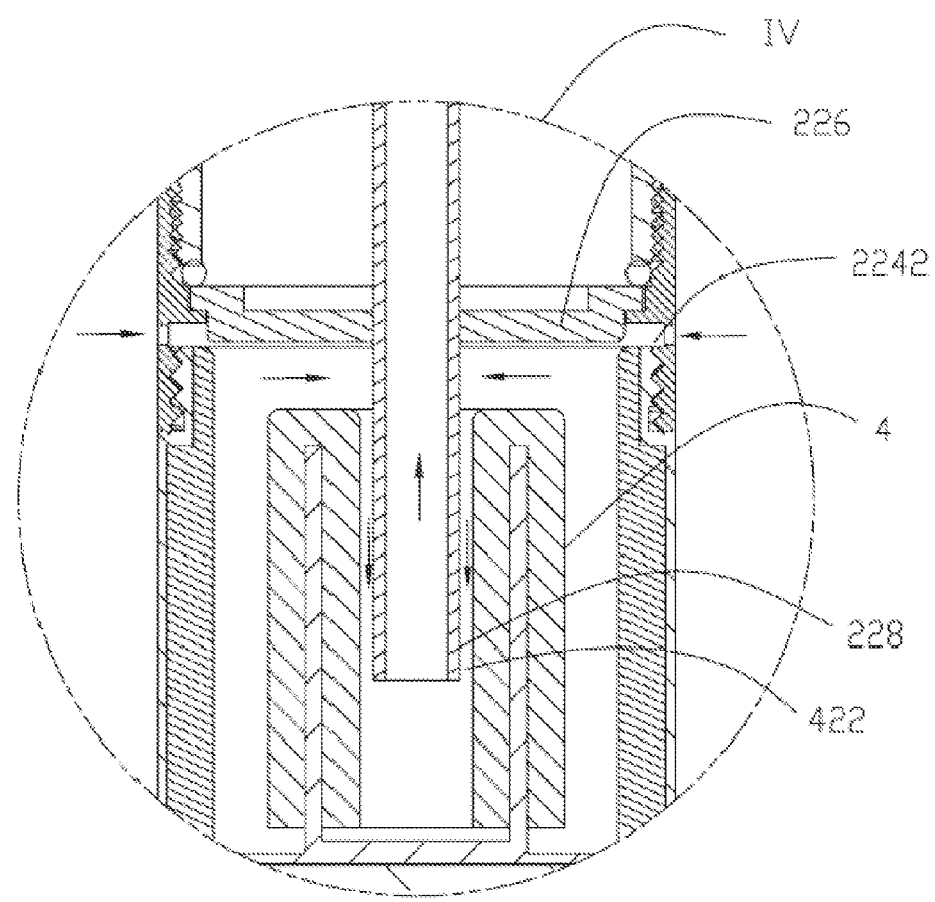
FIG. 4 is a partially enlarged view of area IV of FIG. 1, with air flow direction shown.

Referring to FIG. 4, a direction of the air flow is shown. The air enters the air inlet 2242, flows through a gap between the tobacco block 4 and the thermal baffle 226, passes through a first air passage between the tobacco block 4 and the air pipe 228, flows into the air pipe 228, and then reaches the mouth of the user. The tobacco block 4 may be made of tobacco leaf material or fragrance material. The tobacco leaf material may be selected from the group consisting of flue-cured tobacco, burley tobacco, and aromatic tobacco.

The aerosol formed by the aerosol generating device of the present embodiment taste good. In addition, both of the inner surface and the outer surface of the heating wall heats the tobacco block. Therefore, heating speed of the tobacco block 4 is high, and heat efficiency of the aerosol inhalation device is high.

Figure 5:
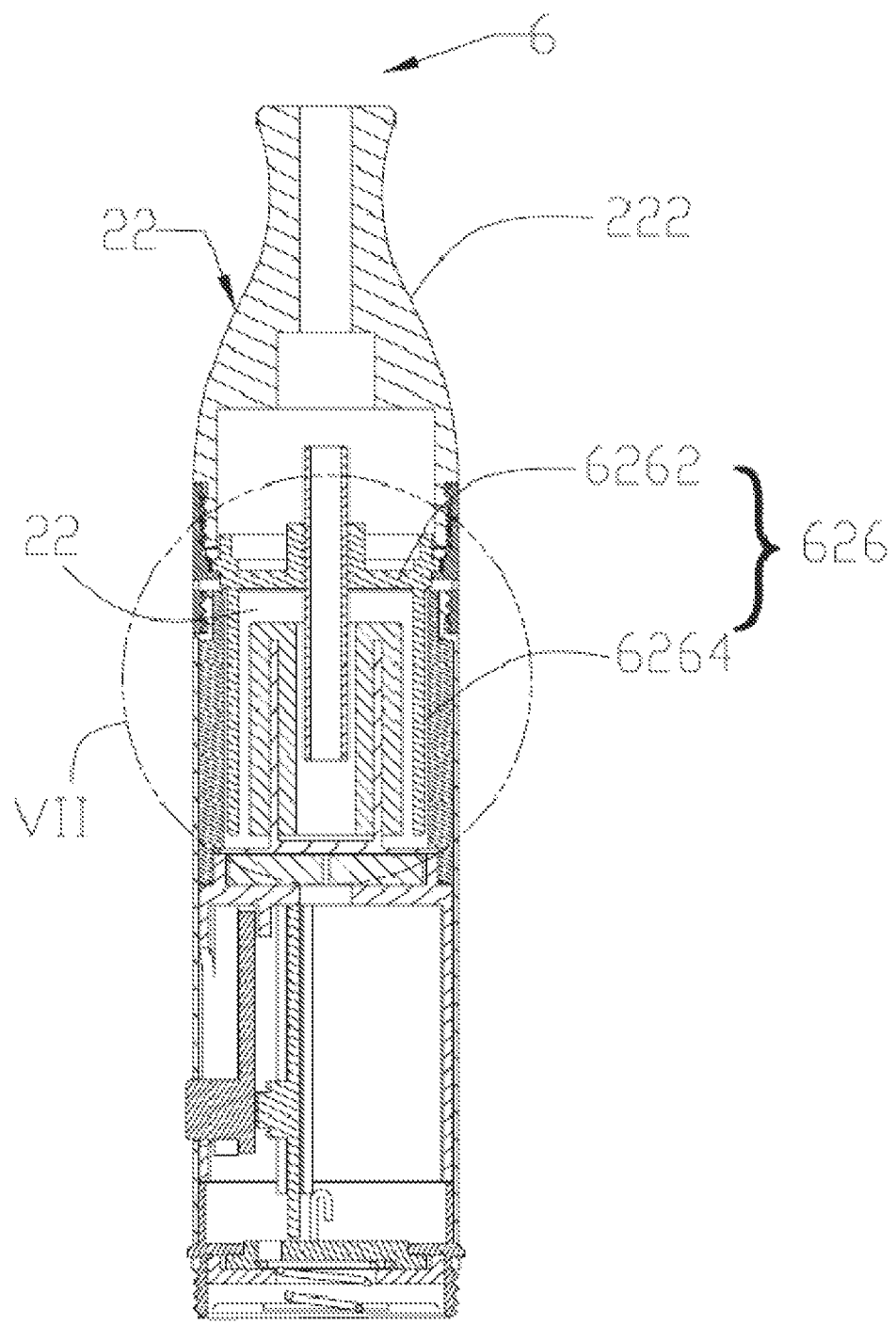
FIG. 5 is a cross-section view of an aerosol generating device according to a second embodiment, including a thermal baffle.
Figure 6:
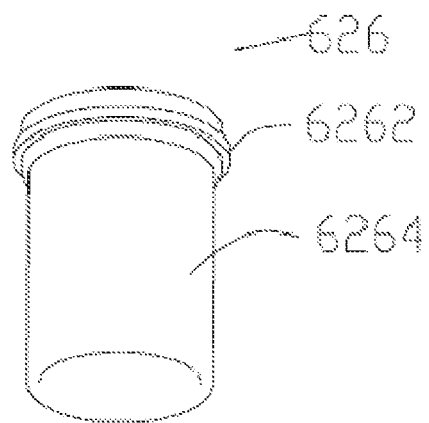
FIG. 6 is a perspective view of the thermal baffle of FIG. 5.
Figure 7:
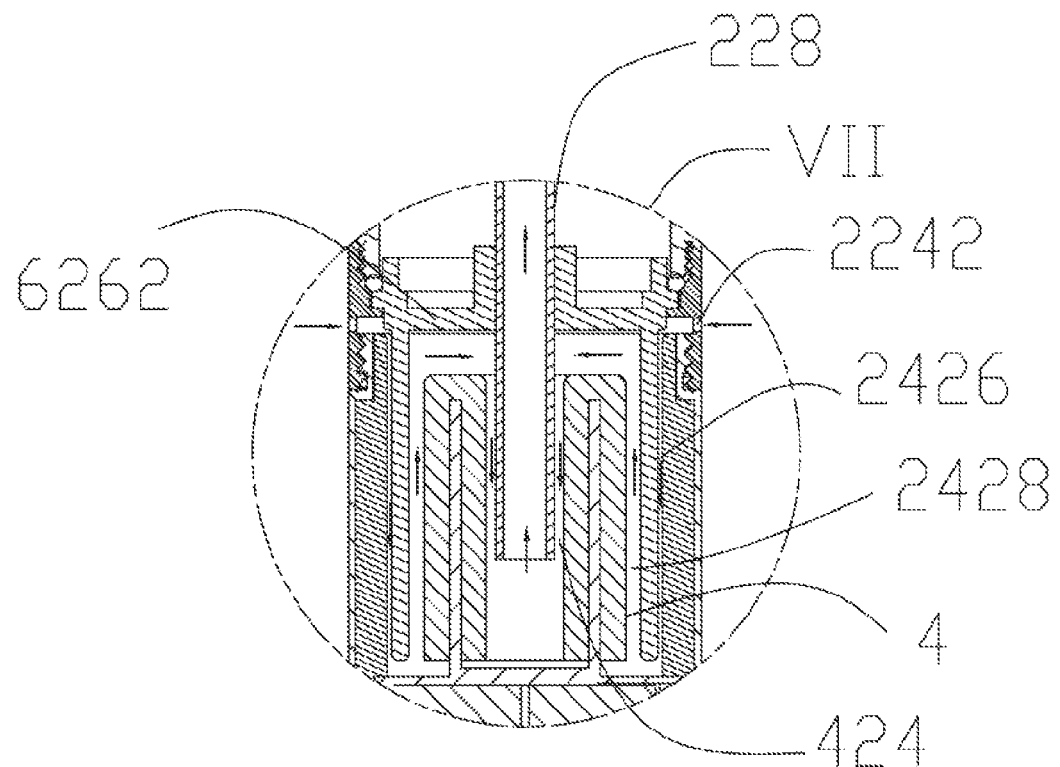
FIG. 7 is a partially enlarged view of area VII of FIG. 5, with air flow direction shown.

Referring to FIGS. 5-7, an aerosol generating device 6 according to a second embodiment is shown. The aerosol generating device 6 is similar to the aerosol generating device 2, and differs in that the thermal baffle 626 includes a main body 6262 and a cylindrical guiding part 6264 perpendicularly extending from the main body 6262. The guiding part 6264 inserts the atomizing chamber 242. A second air passage 2426 is defined between the guiding part 6264 and the heat insulation ring 246 to guide air flowing from the air inlet 2242 toward the circuit board assembly 26, and a third air passage 2428 is defined between the guiding part 6264 and the tobacco block 4 to guide the air flowing from the circuit board assembly 26 toward the mouthpiece assembly 22. The guiding part 6264 is configured for guiding the air to proceed along a circuitous path before reaching the mouth of the user. Accordingly, the tobacco smell and the fragrance smell can be mixed fully and evenly. Specifically, referring to FIG. 7, the air enters the air inlet 2242, flows along the second air passage 2426 and the third air passage 2428, and a gap between an end of the tobacco block 4 and the main body 6262, proceeds along a fourth air passage 424 between an inner surface of the tobacco block 4 and the air pipe 228, and finally reaches the mouth of the user via the mouthpiece 222.

Figure 8:
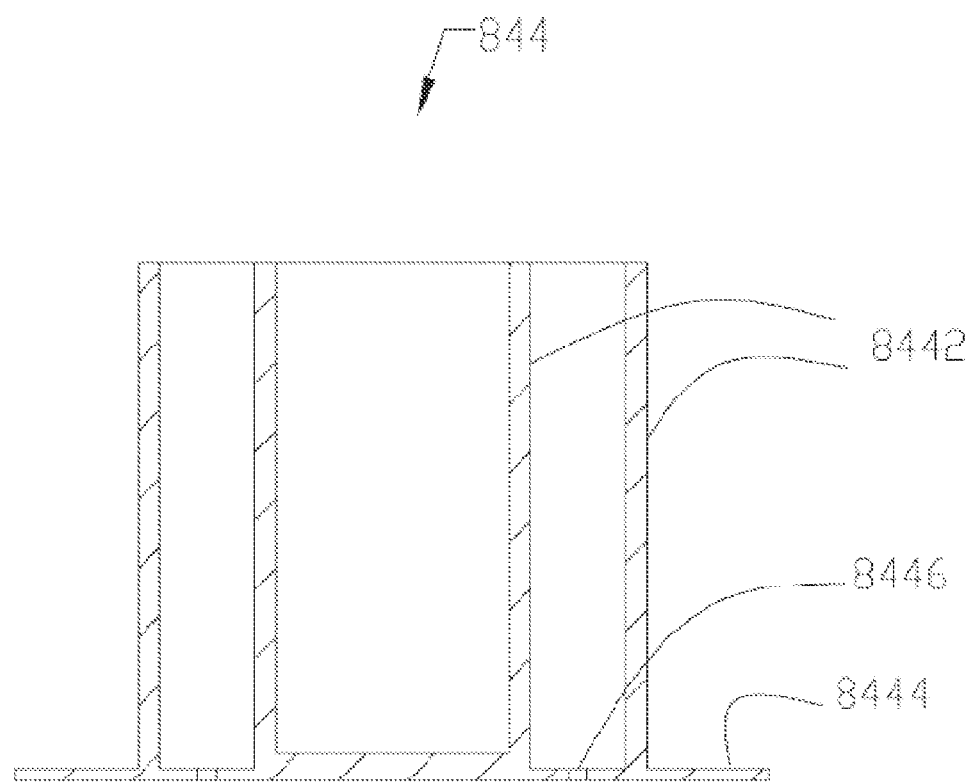
FIG. 8 is a cross-section view of a heating body according to a third embodiment.

Referring to FIG. 8, a heating body 844 according to a third embodiment is shown. The heating body 844 is similar to the heating body 244 of the first embodiment, except that the heating body 844 includes two coaxially cylindrical heating walls 8442 extending from the base 8444. It is to be understood that the shape of the tobacco block coupled with the heating body 844 should be changed accordingly. That is, the tobacco block should include two coaxially cylindrical grooves. In this way, heating surface of the heating body 844 is larger than that in the first embodiment, contact surface between the heating body 844 and the tobacco block also is larger, and heating speed is quicker. Quite usefully, the base 8444 further defines a through hole 8446. It is noteworthy that the heating body 844 may include more than two cylindrical heating walls.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:
1. An aerosol generating device, comprising:
a shell;
a mouthpiece assembly at an end of the shell;
a tobacco block received in the shell; and
an atomizing assembly received in the shell, the atomizing assembly comprising a hollow heating body configured for inserting into the tobacco block and receiving a part of the tobacco block in an inside of the hollow heating body so that the hollow heating body is entirely surrounded by the tobacco block, the heating body comprising an inner surface facing the inside of the hollowing heating body to engage with the part of the tobacco block received in the inside of the hollow heating body, and an outer surface facing away the inside of the hollow heating body to engage with the rest of the tobacco block for heating the tobacco block respectively via the inner surface and the outer surface.

2. The aerosol generating device according to claim 1, further comprising an air pipe, wherein a first end of the air pipe communicates with the mouthpiece assembly, a second end of the air pipe inserts into the tobacco block and resides therein, and a first air passage is defined inside the tobacco block between the tobacco block and the air pipe.

3. The aerosol generating device according to claim 1, further comprising a cylindrical guiding part between the shell and the tobacco block, wherein the guiding part is configured for guiding air to proceed along a circuitous path before reaching the mouthpiece assembly.

4. The aerosol generating device according to claim 3, wherein the guiding part and the shell cooperatively define a second air passage, the guiding part and the tobacco block define a third air passage, the air flows sequentially along the second air passage, and the third air passage.

5. The aerosol generating device according to claim 1, wherein the heating body comprises at least one cylindrical heating wall defining the inner surface and the outer surface respectively at two sides of the at least one cylindrical heating wall.

6. The aerosol generating device according to claim 1, further comprising a connecting assembly at one end of the shell away from the mouthpiece assembly, wherein the connecting assembly is configured for coupling with a power supply.

7. The aerosol generating device according to claim 6, further comprising a heat insulation chamber defined in the shell, wherein the insulation chamber is located between the atomizing assembly and the connecting assembly.

8. The aerosol generating device according to claim 1, wherein the inner surface and the outer surface are in surface contact with the tobacco block.

9. The aerosol generating device according to claim 1, wherein the mouthpiece assembly is detachably coupled to the shell.

10. An aerosol generating device comprising:
a shell;
a mouthpiece assembly at an end of the shell;
a hollow cylindrical tobacco block accommodated in the shell, the tobacco block defines an inside and a groove at one end thereof;
an air pipe comprising a first end of the air pipe communicating with the mouthpiece assembly and a second end of the air pipe inserting into the tobacco block to be located in the inside of the hollow tobacco block, and a first air passage being defined inside the hollow tobacco block between the tobacco block and the air pipe; and
an atomizing assembly received in the shell, the atomizing assembly comprising a hollow heating body configured for inserting into the groove, the heating body comprising an inner surface and an outer surface for heating the tobacco block.

11. The aerosol generating device according to claim 10, further comprising a cylindrical guiding part between the shell and the tobacco block, wherein the guiding part is configured for guiding air to proceed along a circuitous path before reaching the mouthpiece assembly.

12. The aerosol generating device according to claim 11, wherein the guiding part and the shell cooperatively define a second air passage, the guiding part and the tobacco block define a third air passage, the air flows sequentially along the second air passage, and the third air passage.

13. The aerosol generating device according to claim 10, wherein the heating body comprises at least one cylindrical heating wall.

14. The aerosol generating device according to claim 10, further comprising a connecting assembly at one end of the shell away from the mouthpiece assembly, wherein the connecting assembly is configured for coupling with a power supply.

15. The aerosol generating device according to claim 14, further comprising a heat insulation chamber defined in the shell, wherein the insulation chamber is located between the atomizing assembly and the connecting assembly.

16. The aerosol generating device according to claim 10, wherein the inner surface and the outer surface are in surface contact with the tobacco block.

17. The aerosol generating device according to claim 10, wherein the mouthpiece assembly is detachably coupled to the shell.

18. An aerosol inhalation device, comprising:
an aerosol generating device comprising:
a shell;
a mouthpiece assembly at an end of the shell and an air inlet defined between the mouthpiece assembly and the shell;
a tobacco block received in the shell, a first air passage defined inside the tobacco block to guide air entering from the air inlet to flow from the mouthpiece assembly toward the other end of the shell;
an atomizing assembly received in the shell, the atomizing assembly comprising a hollow heating body configured for inserting into the tobacco block for heating the tobacco block; and
a cylindrical guiding part disposed between the shell and the tobacco block, the guiding part and the shell cooperatively define a second air passage therebetween to guide the air entering from the air inlet to flow toward the other end of the shell, the guiding part and the tobacco block cooperatively define a third air passage therebetween to guide the air to flow from the other end of the shell toward the mouthpiece assembly, wherein the air flows sequentially along the second air passage, the third air passage and the first air passage toward the mouthpiece assembly; and
a power supply for providing power to the aerosol generating device.

19. The aerosol inhalation device according to claim 18, further comprising an air pipe, wherein a first end of the air pipe communicates with the mouthpiece assembly, a second end of the air pipe inserts into the tobacco block and resides therein, and the first air passage is defined inside the tobacco block between the tobacco block and the air pipe.

* * * * *